(12) United States Patent
Lal et al.

(10) Patent No.: US 9,970,853 B2
(45) Date of Patent: May 15, 2018

(54) ULTRASONIC HORN ACTUATED MICROPROBES BASED SELF-CALIBRATING VISCOSITY SENSOR

(75) Inventors: Amit Lal, Ithaca, NY (US); Ramkumar Abhishek, Mountain View, CA (US)

(73) Assignee: Cornell University, Ithaca, NY (US)

( * ) Notice: Subject to any disclaimer, the term of this patent is extended or adjusted under 35 U.S.C. 154(b) by 1216 days.

(21) Appl. No.: 13/810,648

(22) PCT Filed: Jul. 14, 2011

(86) PCT No.: PCT/US2011/044032
§ 371 (c)(1),
(2), (4) Date: Apr. 30, 2013

(87) PCT Pub. No.: WO2012/009550
PCT Pub. Date: Jan. 19, 2012

(65) Prior Publication Data
US 2013/0205875 A1   Aug. 15, 2013

Related U.S. Application Data

(60) Provisional application No. 61/365,159, filed on Jul. 16, 2010.

(51) Int. Cl.
*G01N 11/16* (2006.01)
*G01N 29/036* (2006.01)
*G01N 29/24* (2006.01)

(52) U.S. Cl.
CPC ........... *G01N 11/16* (2013.01); *G01N 29/036* (2013.01); *G01N 29/2437* (2013.01); *G01N 2291/02818* (2013.01)

(58) Field of Classification Search
CPC ..................................................... G01N 11/16
(Continued)

(56) References Cited

U.S. PATENT DOCUMENTS 5,728,089 A    3/1998  Lal et al.
6,638,249 B1 * 10/2003 Lal ..................... A61B 5/1411
                                                      604/151
(Continued)

FOREIGN PATENT DOCUMENTS

WO    2008151328 A2   12/2008

OTHER PUBLICATIONS

Abhishek Ramkumar et al., "Silicon ultrasonic horn actuated microprobes based self-calibrating viscosity sensor", MEMS2010 pp. 991-994, Jan. 24-28.*
(Continued)

*Primary Examiner* — Paul West
(74) *Attorney, Agent, or Firm* — Perkins Coie LLP

(57) ABSTRACT

An ultrasonic or acoustic viscosity sensor or viscometer is provided that can be used to accurately measure viscosity for fluid samples of less than 1 µl in volume. Methods for measuring viscosity for fluid samples of less than 1 µl in volume are also provided. The viscosity sensor and methods based thereon enable simultaneous measurement of bulk and dynamic (shear-rate dependent) viscosity of a non-Newtonian fluid. Bulk and dynamic viscosity of the non-Newtonian fluid can be measured simultaneously without separating constituents of the fluid, and thus distinguishing the effect of constituents on the viscosity. Dynamic viscosity of the non-Newtonian fluid can be estimated at varying shear rates, to study the deformability of the constituents of the fluid as a function of shear rate.

33 Claims, 10 Drawing Sheets

Figure 1:
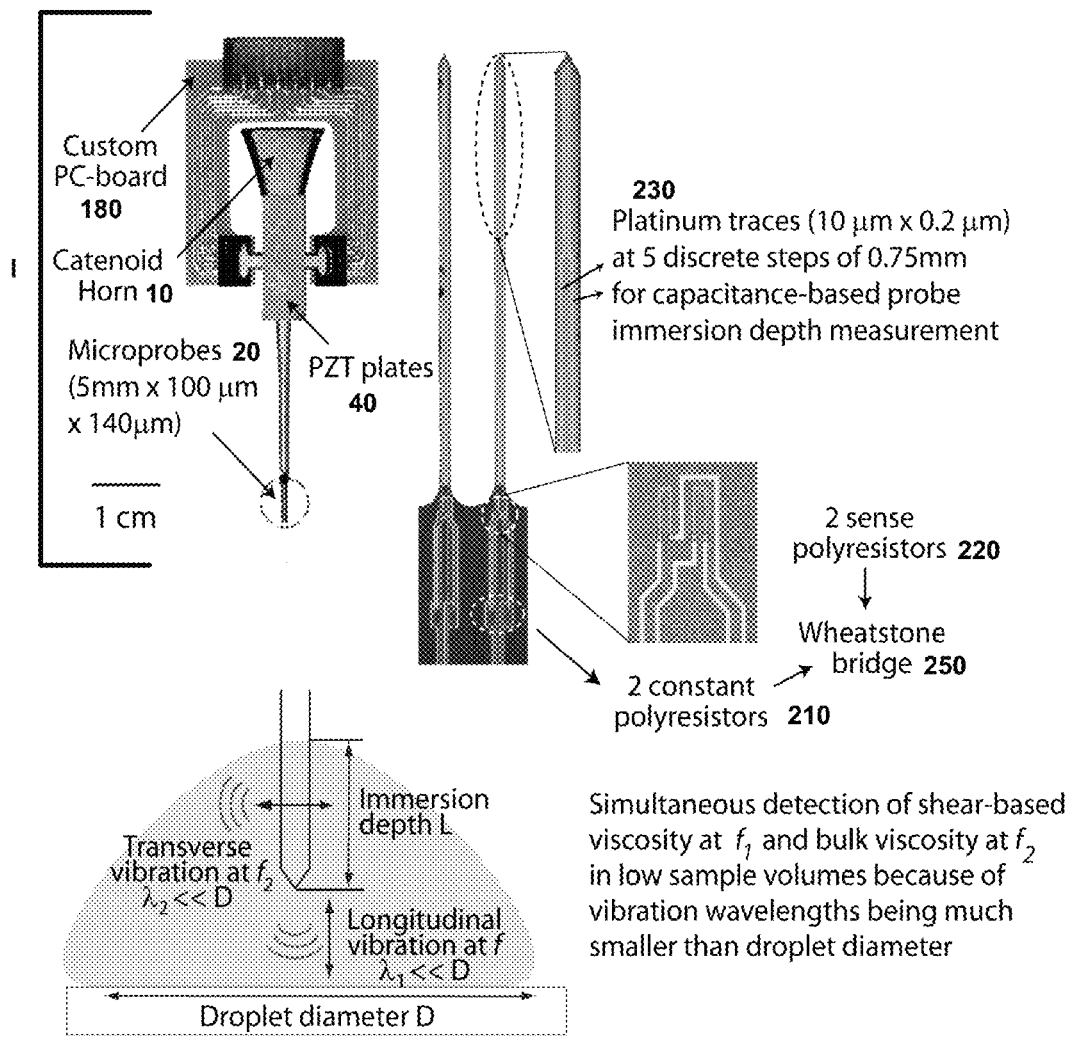

(58) Field of Classification Search
USPC ....... 73/54.41, 54.01, 54.23–54.25; 600/552, 600/553, 561, 587; 604/65–67; 606/169
See application file for complete search history.

(56) References Cited

U.S. PATENT DOCUMENTS

| | | | | |
|---|---|---|---|---|
| 6,845,663 | B2* | 1/2005 | Lopatin | G01F 23/2967 73/290 V |
| 6,869,420 | B2* | 3/2005 | Lal | A61B 5/1411 604/151 |
| 6,923,790 | B2* | 8/2005 | Lal | A61B 5/1411 128/200.16 |
| 8,197,418 | B2* | 6/2012 | Lal | A61B 5/0053 600/552 |
| 2004/0204680 | A1 | 10/2004 | Lal et al. | |
| 2008/0028837 | A1 | 2/2008 | Djakov et al. | |
| 2008/0092647 | A1* | 4/2008 | Kumazawa | G01F 23/268 73/304 C |
| 2012/0111107 | A1* | 5/2012 | Shimura | G01F 23/268 73/304 C |

OTHER PUBLICATIONS

Chen et al.,Ultrasonincally Actuated Silicon Microprobes for Cardiac Signal Recording, IEEE Tensaction on Biomedical Engineering, vol. 53, No. 8, Aug. 2006.*

Ramkumar et al., Silison Ultrasoninc Horn Driven Microprobe Viscometer, 2006 IEEE Ultrasonic Symposium.*

Ramkumar, A. et al., "Silicon Ultrasonic Horn Actuated Microprobes Based Self-Calibrating Viscosity Sensor," MEMS pp. 991-994, Jan. 2010.

International Search Report and Written Opinion for International Application No. PCT/US2011/044032, dated Mar. 13, 2012, 8 pages.

First Office Action for Chinese Patent Application No. 201180044775.3, dated Mar. 21, 2014, 15 pages.

Second Office Action for Chinese Patent Application No. 201180044775.3, dated Feb. 12, 2015, 4 pages.

Wanamethee, S.G. et al., "Circulating inflammatory and hemostatic biomarkers are associated with risk of myocardial infarction and coronary death, but not angina pectoris, in older men", J. Thromb. Haemost, vol. 7, 2009, pp. 1605-1611.

Somer, T. et al., "Disorders of Blood Viscosity", Annals of Medicine, vol. 25, 1993, pp. 31-39.

Tamariz, L.J. et al., "Blood Viscosity and Hematocrit as Risk Factors for Type 2 Diabetes Mellitus The Atherosclerosis Risk in Communities (ARIC) Study", Am J. Epidemiol., vol. 168, No. 10, pp. 1153-1160, 2008.

Son et al., "A multifunctional silicon-based microscale surgical system", Sensors and Actuators A, vol. 91, issue 3, 2001, pp. 351-356.

Rosenson, A. et al., "Distribution of blood viscosity values and biochemical correlates in healthy adults", Clin. Chem., vol. 42, No. 8, 1996, pp. 1189-1195.

Rosenblum, W.I., "In vitro Measurements of the Effects of Anticoagulants on the Flow Properties of Blood: The Relationship of these Effects to Red Cell Shrinkage," Blood, vol. 31, No. 2, 1968, 234-241.

Riesch, C. et al., "Characterizing Vibrating Cantilevers for Liquid Viscosity and Density Sensing," J. Sensors, vol. 2008, Article ID 697062, pp. 1-9.

Muramatsu, H. et al., "Piezoelectric Resonator as a Chemical and Biochemical Sensing Device," Sens. Act., A21- A23, 1990, pp. 362-368.

Martin, B.A. et al., "Viscosity and Density Sensing with Ultrasonic Plate Waves," Sens. Act., A21-A23, 1990, pp. 704-708.

Lal, "Micromachined Silicon Ultrasonic Longitudinal Mode Actuators: Theory and Applications to Surgery, Pumping, and Atomization", Ph.D. Dissertation, University of California, Berkeley, 1996, 253 pages.

Lal et al., "Silicon microfabricated horns for power ultrasonics", Sensors and Actuators, vol. A54, 1996, pp. 542-546.

Kanazawa, et al., "Frequency of a Quartz Microbalance in Contact with Liquid", Anal. Chem, vol. 57, 1985, pp. 1770-1771.

Etchart, I., et al., "MEMS sensor for density-viscosity sensing in a low-flow microfluidic environment", Sensors and Actuators A 141, 2008, pp. 266-275.

Cheng, T.-J., et al., "A piezoelectric quartz crystal sensor for the determination of coagulation time in plasma and whole blood", Biosens. and Bioelec., vol. 13, No. 2, 1998, pp. 147-156.

Chen et al., 'Integrated Pressure and Flow Sensor in Silicon-based Ultrasonic Surgical Actuator, IEEE Ultrasonics Symposium, 2001, pp. 1373-1376.

Bandey, L. et al., "Blood rheological characterization using the thickness-shear mode resonator", Biosensors and Bioelectronics, vol. 19, 2004, pp. 1657-1665.

Devereux, R.B. et al., "Possible Role of Increased Blood Viscosity in the Hemodynamics of Systemic Hypertension," Am. J. Cardiol., vol. 85, 2000, pp. 1265-1268.

* cited by examiner

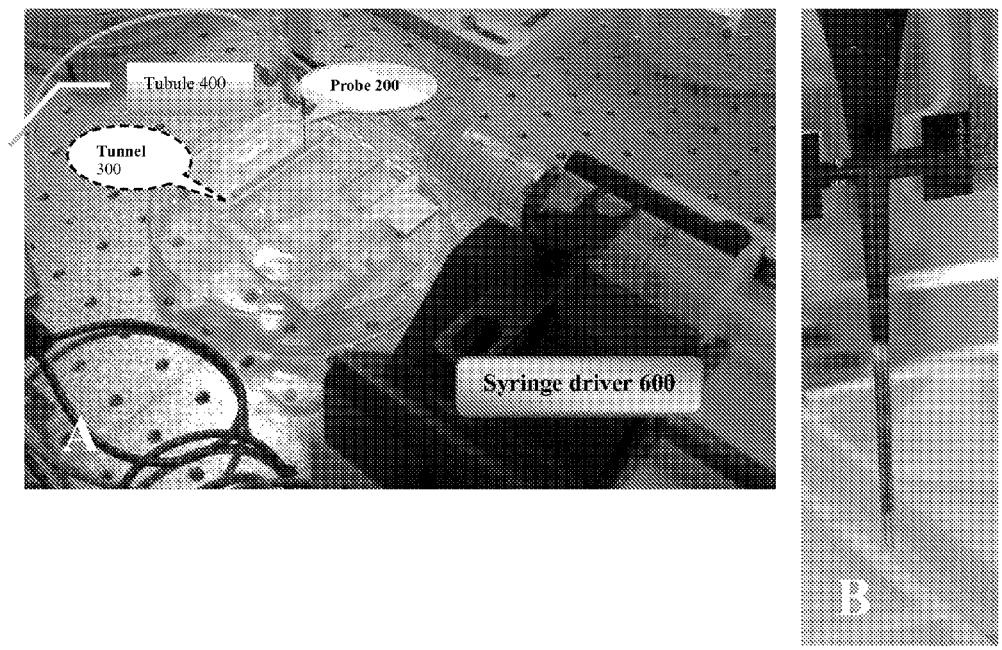
FIGS. 9A-B
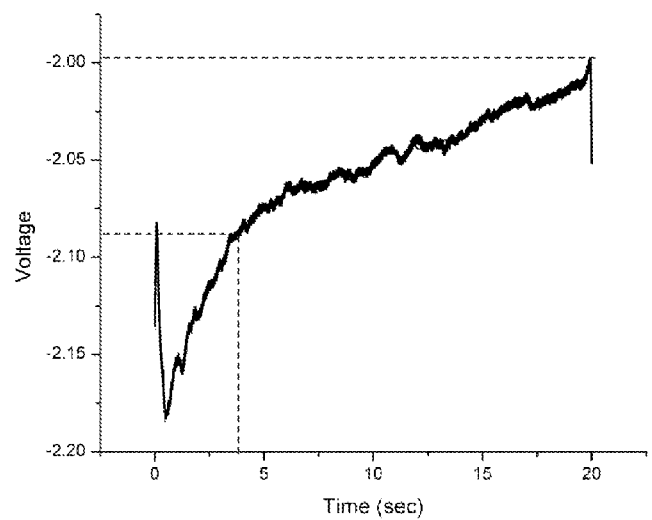
FIG. 10

ULTRASONIC HORN ACTUATED MICROPROBES BASED SELF-CALIBRATING VISCOSITY SENSOR

CROSS-REFERENCE TO RELATED APPLICATIONS

This application is a 35 USC § 371 National Stage application of, and claims priority of, international application Serial No. PCT/US2011/044032 filed Jul. 14, 2011, which further claims priority to and the benefit of U.S. provisional patent application Ser. No. 61/365,159, entitled "Ultrasonic horn actuated microprobes based self-calibrating viscosity sensor," filed Jul. 16, 2010, which is incorporated herein by reference in its entirety.

STATEMENT REGARDING FEDERALLY SPONSORED RESEARCH OR DEVELOPMENT

The disclosed invention was made with government support under Contract No. 5R01HL073644-0, entitled "MEMS sensors for arrhythmia detection and intervention" from the National Institutes of Health. The government has rights in this invention.

1. TECHNICAL FIELD

The present invention relates to fluid viscosity and flow sensors. The invention also relates to devices for measuring viscosity and flow of blood.

2. BACKGROUND OF THE INVENTION

Medical diagnosis of disease often requires determining the viscosity of body fluids, very importantly that of blood. Blood rheology in vivo can be used for prediction of blood flow through capillaries of varying sizes, while its in vitro rheology can be used for diagnosis and monitoring of diseases. Also, changes in blood rheology have been seen to contribute to or aggravate cardiovascular disorders such as myocardial infarction and hypertension. Clinical hemorheological tests measure the red blood cell (RBC or erythrocyte) aggregation by the erythrocyte sedimentation rate (ESR) and the plasma viscosity. Physiological conditions leading to alteration of plasma proteins (such as fibrinogen) results in a change in the ESR and plasma viscosity. Correlation to blood rheology can be used as a good indicator for prognosis, diagnosis and/or monitoring disease processes such as cancer, cardiovascular disease, etc. For example, inflammatory biomarkers (fibrinogen) and plasma viscosity have been observed to be significantly associated with death due to myocardial infarction or coronary heart disease. Incidence of type 2-diabetes has been shown to be strongly related to high whole blood viscosity (WBV), thus allowing a measure of blood viscosity to be a prognosis tool. Also, monitoring plasma viscosity can help in the prediction and diagnosis of plasma hyperviscosity syndrome and sickle cell disease. Additionally, a measure of blood viscosity can help in monitoring interventions to alter blood viscosity such as diet, alcohol, pharmaceuticals etc.

Viscosity meters use various fluid-mechanical instruments to move the fluid applying a shear stress layer which generates a viscosity modified damping or flow, which are measured electronically, optically, etc. One device known in the art that can be used to measure viscosity is a mechanical resonator loaded with a liquid. The implied velocity field into the fluid from the resonator results in bulk and shear motion induced damping, both affecting the quality factor of the resonance, the resonance frequency, and the resonant motion amplitude, among other variables. One aspect of medical relevancy of blood viscosity is the fluidic resistance upon parts moving at displacement greater than several red blood-cell diameters. A viscosity sensor for blood should be able to move the blood cells individually such that the interaction of the blood cells with the plasma is sampled adequately. This greatly limits the use of high frequency MEMS resonators where displacements are in the deep sub-micron regime, for estimating viscosity by monitoring the viscous damping. On the opposite extreme are low frequency resonant devices that can become bulky owing to the low spring constant k or high mass m required to make the resonant frequency low. At low frequencies the size of the resonators approaches that of commercial tabletop viscometers requiring tens of milliliters of blood.

Furthermore, with micro or millimeter scale resonators, the total contact area of the sample with the probes strongly determines the loss of mechanical energy into the fluid from the actuator. Hence, it is important to measure the contact area to measure viscosity accuracy. In typical sensors, the sensor area is typically much smaller than the fluid volume completely submerging the sensor in the fluid. However, in cases where tiny amounts of samples are present, this condition is hard to maintain.

There is therefore a need in the art for a fluid viscosity and flow sensor for use as a prognosis, diagnosis and/or monitoring device. There is also a need for an instrument to measure body fluid viscosity at varying shear rates in real-time (for example, before a blood sample coagulates) using <1 µl fluid samples. Such an instrument, together with other biosensor(s) such as glucose sensors for diabetic patients, could serve as an invaluable tool for rapid monitoring of an individual's physiological function.

Citation or identification of any reference in Section 2, or in any other section of this application, shall not be considered an admission that such reference is available as prior art to the present invention.

3. SUMMARY OF THE INVENTION

An ultrasonic or acoustic viscosity sensor 1 for measuring fluid viscosity or fluid flow of a fluid in real time is provided. In one embodiment, the viscosity sensor comprises:
   an ultrasonic or acoustic actuator 10;
   at least one microprobe 20 (also referred to herein as a "probe") for sensing ultrasound induced motion; and
   means for generating motion via coupling between the actuator and the at least one microprobe.

In one embodiment, the ultrasonic or acoustic viscosity sensor comprises a substrate.

In another embodiment, the ultrasonic actuator couples motion to the at least one microprobe through the substrate.

In another embodiment, the actuator is driven at at least one of its mechanical resonance frequencies.

In another embodiment, the at least one microprobe is driven at at least one of its mechanical resonance frequencies by the actuator.

In another embodiment, the actuator is a silicon ultrasonic longitudinal mode actuator.

In another embodiment, the actuator is actuated by at least one piezoelectric element.

In another embodiment, the piezoelectric element is adhesively attached.

In another embodiment, the piezoelectric element is a thin piezoelectric film.

In another embodiment, the silicon ultrasonic longitudinal mode actuator has varying cross-section for amplifying motion imparted to the at least one microprobe.

In another embodiment, the ultrasonic or acoustic viscosity sensor operates in acoustic frequencies between 10 Hz to 20 kHz.

In another embodiment, the ultrasonic or acoustic viscosity sensor operates in mid ultrasonic frequencies between 20 kHz to 500 kHz.

In another embodiment, the ultrasonic or acoustic viscosity sensor operates in upper ultrasonic frequencies between 500 kHz to 10 MHz.

In another embodiment, the ultrasonic or acoustic viscosity sensor generates high amplitude (e.g., 1-10 μm) motion in the fluid of interest.

In another embodiment, the ultrasonic or acoustic viscosity sensor comprises means for measuring damping of the mechanical vibrations of the at least one microprobe in the fluid of interest.

In another embodiment, the means for measuring damping of the mechanical vibrations comprises at least two strain gauges (e.g., polysilicon strain gauges) or piezoresistors located at the junction of the actuator 10 and the microprobes 20, wherein at least one of the strain gauges or piezoresistors measures the amplitude of motion of the at least one microprobe and wherein at least one of the strain gauges or piezoresistors measures the motion of the actuator.

In another embodiment, at least one of the strain gauges or piezoresistors is a polysilicon resistor In another embodiment, at least one of the strain gauges or piezoresistors is integrated (or positioned) at the junction of the actuator 10 (e.g., silicon horn actuator) and the microprobe.

In another embodiment, at least one of the strain gauges or piezoresistors has a nominal resistance of about 10 kΩ.

In another embodiment, the ultrasonic or acoustic viscosity sensor comprises means 230 for measuring immersion depth of the microprobe in the fluid.

In another embodiment, the means for measuring immersion depth is based on measurement of capacitance between two electrodes.

In another embodiment, the ultrasonic or acoustic viscosity sensor comprises a capacitance-based immersion depth sensor.

In another embodiment, the capacitance-based immersion depth sensor enables self-calibration of the viscosity sensor.

In another embodiment, the capacitance-based immersion depth sensor comprises means for distance-coding capacitance.

In another embodiment, the means for distance-coding capacitance is formed by at least two metal traces on the capacitance-based immersion depth sensor.

In another embodiment, the capacitance is measured as a function of frequency to extract the dielectric constant of the fluid as a function of frequency.

In another embodiment, the ultrasonic or acoustic viscosity sensor comprises computational circuitry functionally connected to the microprobe.

In another embodiment, the ultrasonic or acoustic viscosity sensor is integrated into a strip format.

In another embodiment, the strip format is a blood-glucose measurement strip

In another embodiment, the ultrasonic or acoustic viscosity sensor comprises:
a silicon horn 15;
a piezoelectric actuator element 16; and
a multi-sensor microprobe 20 for sensing ultrasound induced motion,
wherein:
the multi-sensor multiprobe comprises:
at least one polysilicon strain gauge or piezoresistor 200 connected in a
Wheatstone bridge 250 configuration, and
a capacitance-based immersion depth sensor 230.

In a specific embodiment, the actuator comprises the silicon horn 15 and the piezoelectric actuator element 16.

In one embodiment, the ultrasonic or acoustic viscosity sensor is mid-frequency resonant, e.g., 20-500 kHz.

In another embodiment, the ultrasonic or acoustic viscosity sensor is high-frequency resonant, e.g., 500 kHz-10 MHz.

In another embodiment, the ultrasonic or acoustic viscosity sensor generates high amplitude motion. In a specific embodiment, the amplitude of the high amplitude motion is 1 μm or greater.

In another embodiment, the ultrasonic or acoustic viscosity sensor comprises at least one multi-sensor microprobe.

In another embodiment, the at least one multi-sensor microprobe comprises a plurality of strain gauges or piezoresistors.

In another embodiment, the microprobe comprises a plurality of capacitance-based immersion depth sensors.

In another embodiment, the multi-sensor microprobe comprises a plurality of capacitance-based immersion depth sensors.

A method for measuring fluid viscosity or fluid flow of a fluid of interest is also provided. In one embodiment, the method comprises the steps of:
providing the ultrasonic or acoustic viscosity sensor of claim 1; and
measuring viscous damping of non-linear flexural vibrations of the microprobe induced by the λ/2 longitudinal resonance of the silicon horn. The fluid viscosity can then be calculated using the viscous damping measurement(s) as described herein.

In one embodiment, the non-linear flexural vibrations of the microprobe comprise longitudinal and flexural oscillating motions.

In another embodiment, the step of measuring viscous damping comprises measuring viscous damping at multiple frequencies.

In another embodiment, a first of the multiple frequencies is the actuator longitudinal mode frequency and a second of the multiple frequencies is the microprobe resonance frequency.

In another embodiment, the microprobe resonance is excited parametrically at a frequency different then the actuation frequency for simultaneous dual frequency actuation. shear (non-linear vibration) damping and bulk (silicon horn's longitudinal resonance) damping at two different frequencies, thereby simultaneously measuring the static (bulk) viscosity and dynamic (shear-rate dependent) viscosity of the fluid of interest.

In another embodiment, the method comprises calculating the frequency and magnitude of a signal corresponding to the multi-frequency excitation from the Fast Fourier Transform (FFT) of the amplified Wheatstone bridge voltage signal corresponding to the motion of a cantilever of the at least one microprobe.

In another embodiment, the method comprises the step of calibrating immersion depth. In a specific embodiment, the calibrating step comprises measuring capacitance at discrete steps.

In another embodiment, the method comprises the step of determining the shear decay length (δ) at the actuator resonance, wherein δ is given by $$\delta = \left(\frac{2\eta}{\omega\rho}\right)^{\frac{1}{2}}$$

where η and ρ are the fluid viscosity and density, respectively, and ω=2πf is the angular frequency of flexural vibration of the at least one microprobe In another embodiment, the method comprises the step of measuring the viscosity of the fluid of interest at different shear rates. In one embodiment, this step comprises varying piezoelectric transducer (PZT) actuation voltage.

In another embodiment, the method comprises the step of assessing coagulation time of the fluid of interest (e.g., blood).

In another embodiment, the method comprises the step of measuring the coagulation of the fluid of interest (e.g., blood).

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. An embodiment of the viscosity sensor 1. Top left: Photograph of the viscosity sensor 1. Piezoresistors 200 (in this embodiment, ~9 kΩ) are located at the junction of an actuator 10 (in this embodiment, a catenoid silicon horn 10) and a pair of microprobes 20 to sense ultrasound-induced strain oscillations. PZT plates 40 (piezoresistive transducer plates). Top right: metal traces 230 (in this embodiment, 10 μm×0.2 μm platinum traces) are located such that there is a capacitor formed between the two wires. The two wires consist of discrete steps along the microprobes, for provided stepped capacitance change along the length of the probe. As the microprobe 20 is inserted in a liquid, the different dielectric constant of the liquid results in increase in capacitance as the probe immersion depth is increased. As the liquid crosses each of the stepped locations, the capacitance change is stepped as well. Since the distance between the steps is known, the position and velocity of insertion can be calibrated from the change in capacitance curves. A second capacitance sensor can be incorporated opposite to the sensor on the opposite side of the probes to provide a differential capacitance measurement. Incorporating multiple electrodes on multiple probes can lead to determination of the meniscus level at each sensor, enabling the measurement of the tilt of the probes with respect to the fluid meniscus. In this embodiment, two polysilicon resistors are placed on the actuator side, and two polysilicon resistors are placed on the two probes. The four resistors 200 are connected in a Wheatstone bridge 250 configuration such that change in the resistance due to strain in the probes is measured differentially compared to the strain on the actuator side. Bottom: The microprobes can be used for multi-sensing viscosity (bulk and shear) measurements in micro-droplet fluid samples at specific or desired immersion depths. The diagram depicts simultaneous detection of shear-based viscosity at $f_1$, for which the shear viscous depth of a few microns is much smaller than the droplet diameter and bulk viscosity at $f_2$ where the wavelength is typically much larger than the droplet diameter. Custom PC-board 180.

FIGS. 2A-B. A. Frequency spectrum of Wheatstone bridge voltage showing the longitudinal and flexural vibration. B. Two-dimensional laser Doppler vibrometer measurement of microprobe's flexural displacement and surface plot along the length of the microprobes indicating the mode shape with three nodes. The 2-D scan is of z-displacement velocity of microprobe flexural vibration along the probe's length. Two piezo-electric transducers (14.2×5 mm) are driven at a longitudinal resonance of the silicon horn (f=109.8 KHz). The surface plot shows the out-of-plane flexural vibration of the microprobes at 30.4 KHz.

Figure 3:
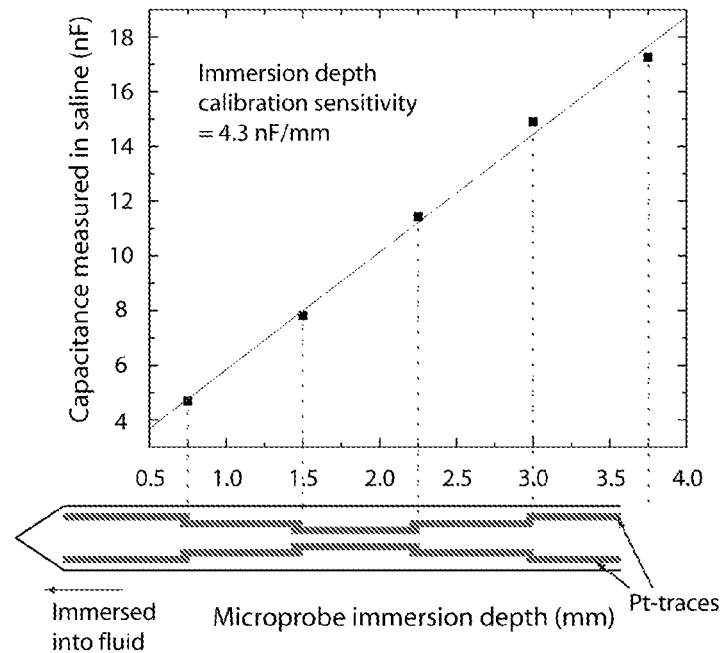

FIG. 3. Capacitance-based calibration of microprobe immersion depth in physiological saline (0.9% w/v NaCl). Platinum traces (10 μm wide and 0.2 μm thick) have discrete steps of 0.75 mm and capacitance is measured at every step.

Figure 4:
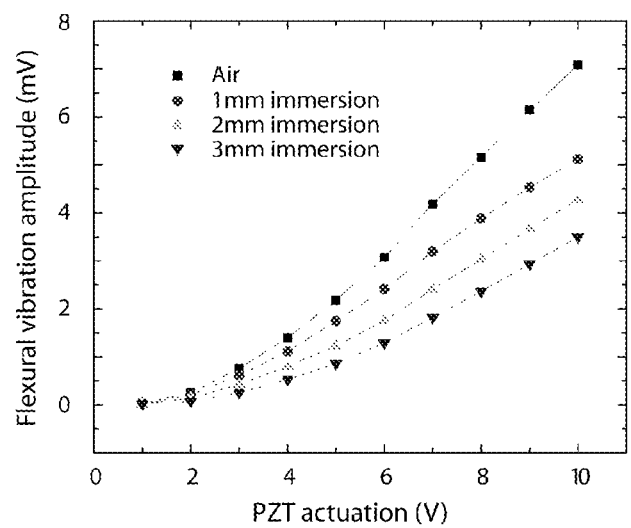

FIG. 4. Amplitude of microprobe flexural vibration in de-ionized (DI) water when compared to air, for increasing PZT actuation voltages at varying immersion depths of microprobe (1-3 mm).

Figure 5:
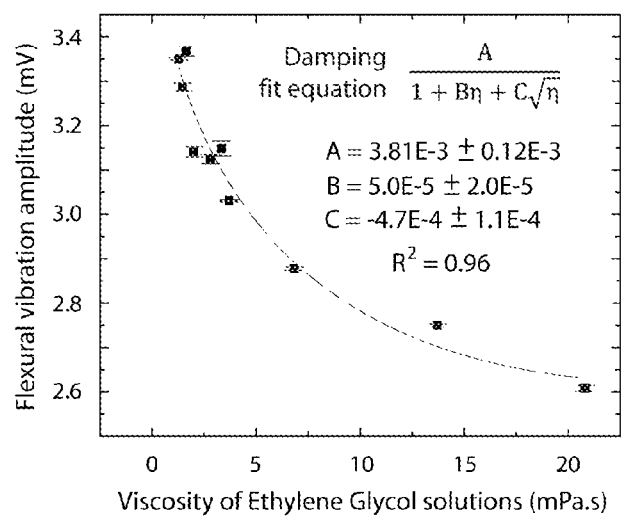

FIG. 5. Damping of microprobe vibration in ethylene glycol solutions (2 mm immersed) of varying viscosities at $8V_{pp}$ PZT actuation. The viscous damping of the microprobe is modeled assuming the immersed part to be an oscillating sphere.

Figure 6:
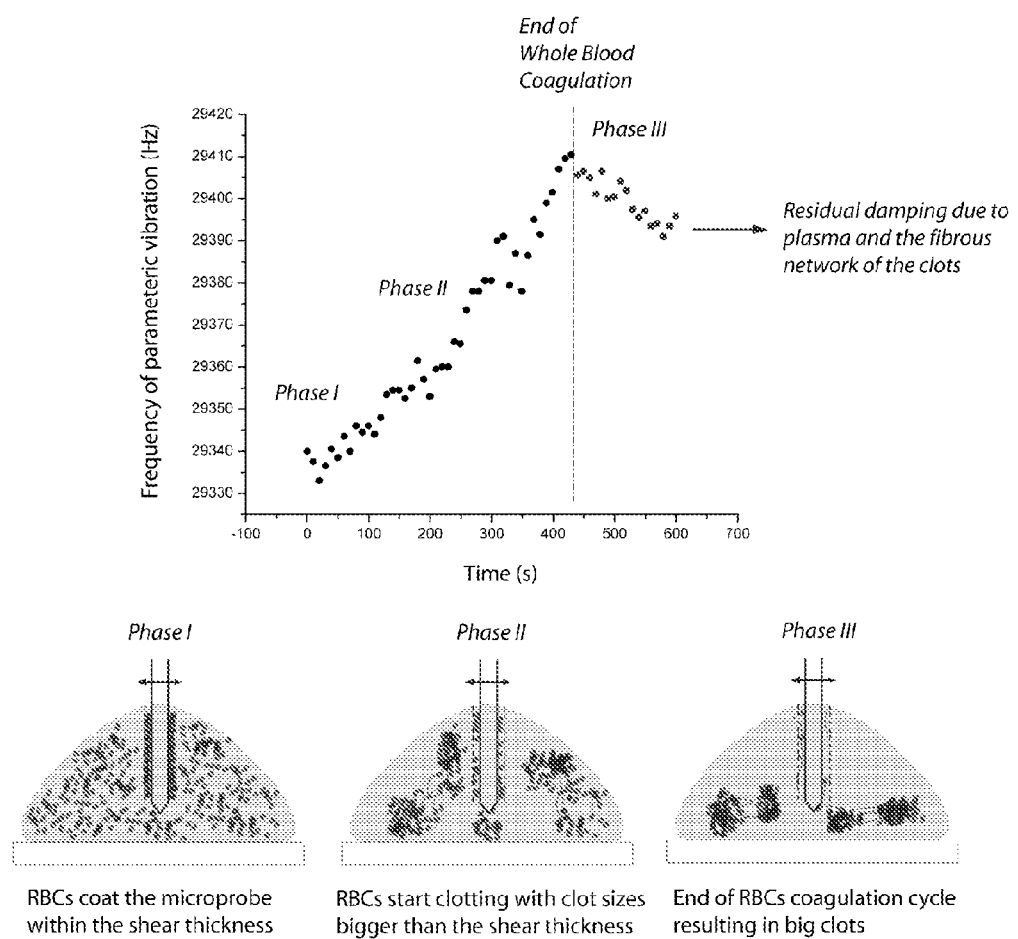

FIG. 6. Frequency variation of microprobe flexural vibration in whole rat blood (~1 mm immersed) at $10V_{pp}$ PZT actuation. Phase I: The red blood cells (RBCs) coat the microprobe within the shear thickness (~4 μm) and load the vibration frequency reducing it. Phase II: The blood starts to coagulate with the RBCs clotting with clot sizes bigger than the shear thickness, thus lessening the loading on the vibration (increasing the frequency). Phase III: End of blood coagulation with the formation of fibrous structures and large clots—the residual damping is due to few RBCs, the plasma and the fibrous network of clots.

Figure 7:
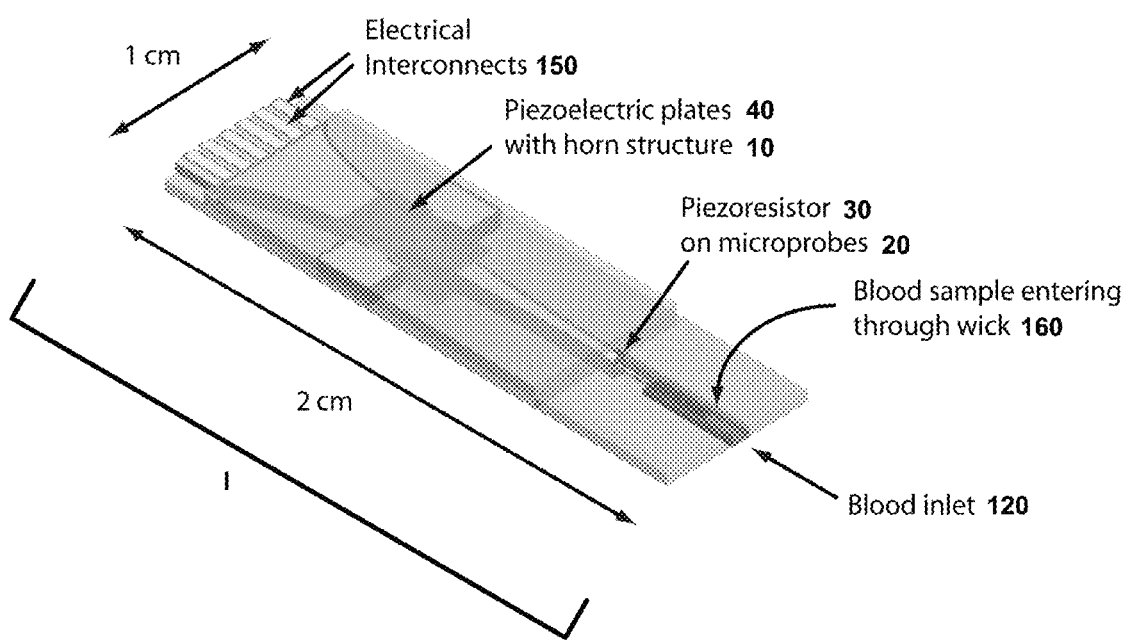

FIG. 7. Another embodiment of the viscosity sensor 1. In this embodiment, the viscosity sensor 1 comprising the microprobes 20 is integrated into a typical strip test, much like those used for blood-glucose measurement. Commercially available glucose strips have a small wicking channel formed by two plastic or paper laminates such the blood is wicked into the strips. Electrical interconnects 150 are provided at the back end of the viscosity sensor 1 for electrochemical measurements. The electrical interconnects 150 can plug into a reader for performing the measurements. The blood enters the chamber with the microprobes 20 through the wick 160. Once the blood is collected, simultaneous measurements of glucose levels and viscosity, and thus PT and PTT coagulation times can be performed. As the blood constituents change as blood plasma evaporates, the levels of the liquid on the probes can be measured continuously to maintain accuracy of viscosity measurement.

Figure 8:
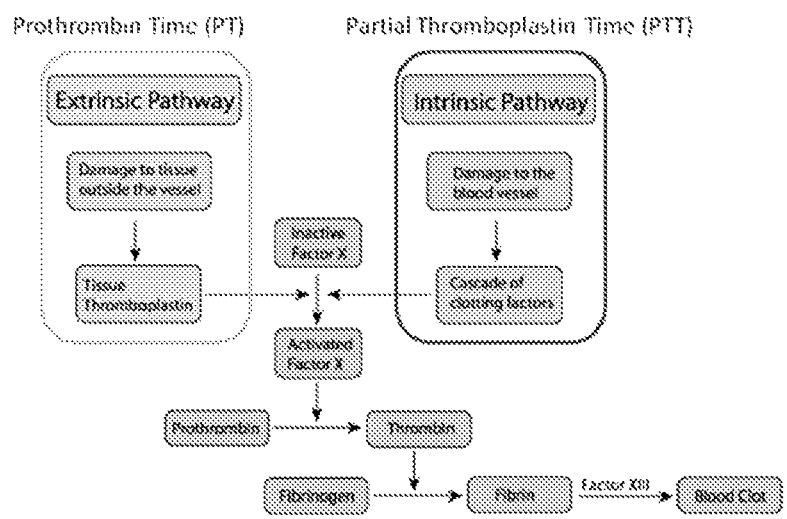

FIG. 8. Blood coagulation tests. Diagram of two hemorheological tests that are blood coagulation tests and that are currently used for diagnosis and monitoring of diseases. Prothrombin Time (PT) test. Partial Thromboplastic Therapy (PTT) test.

FIGS. 9A-B. A. One embodiment of the invention showing measurement of fluid flow inside a channel or tunnel 300 by piezoresistive probes 20. B. ~2 mm of the probe tips is inside the tunnel/channel 300. Tubule 400. Syringe driver 600. See Section 6.2 for details.

FIG. 10. A voltage measurement taken when a channel is filling with water during the experiment described in Section 6.2. System settles in 3.5 sec.

Figure 11:
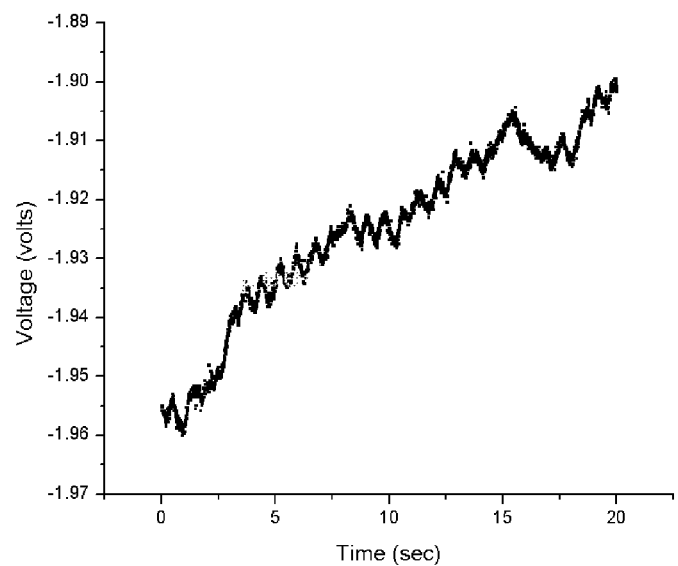

FIG. 11. A voltage measurement taken when a channel is filling with water during the experiment described in Section 6.2. Measurement started after system settlement.

Figure 12:
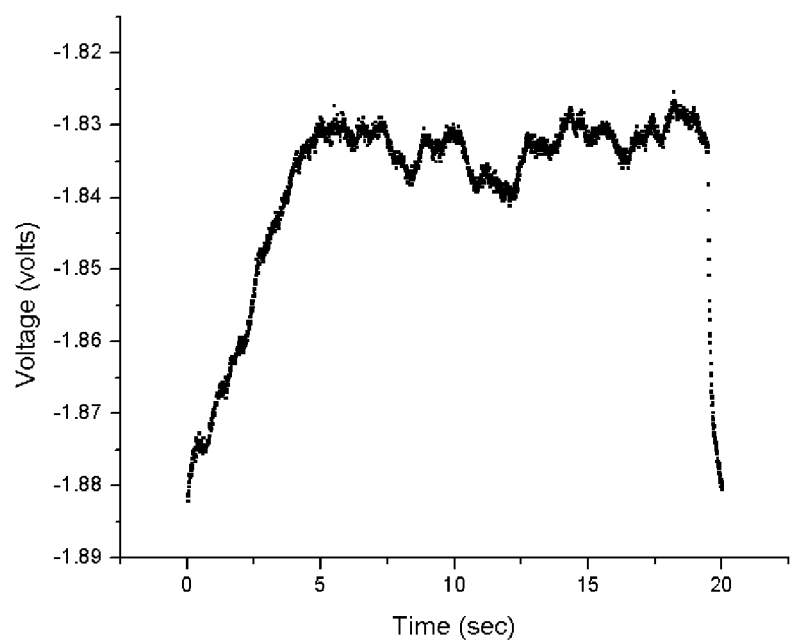

FIG. 12. A voltage measurement taken when the water depth in the channel is constant during the experiment described in Section 6.2.

Figure 13A:
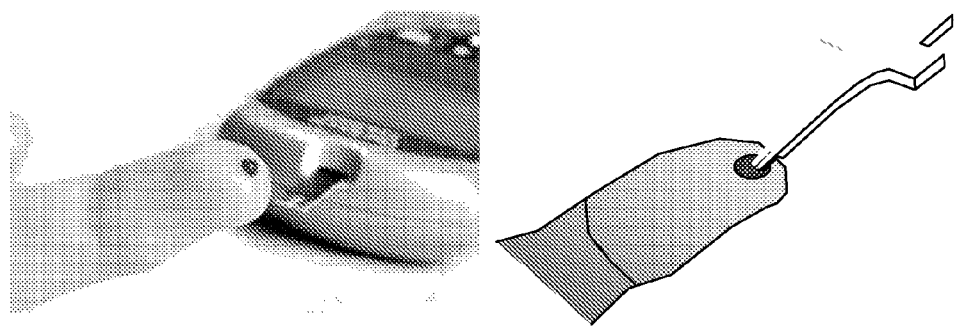
Figure 13B:
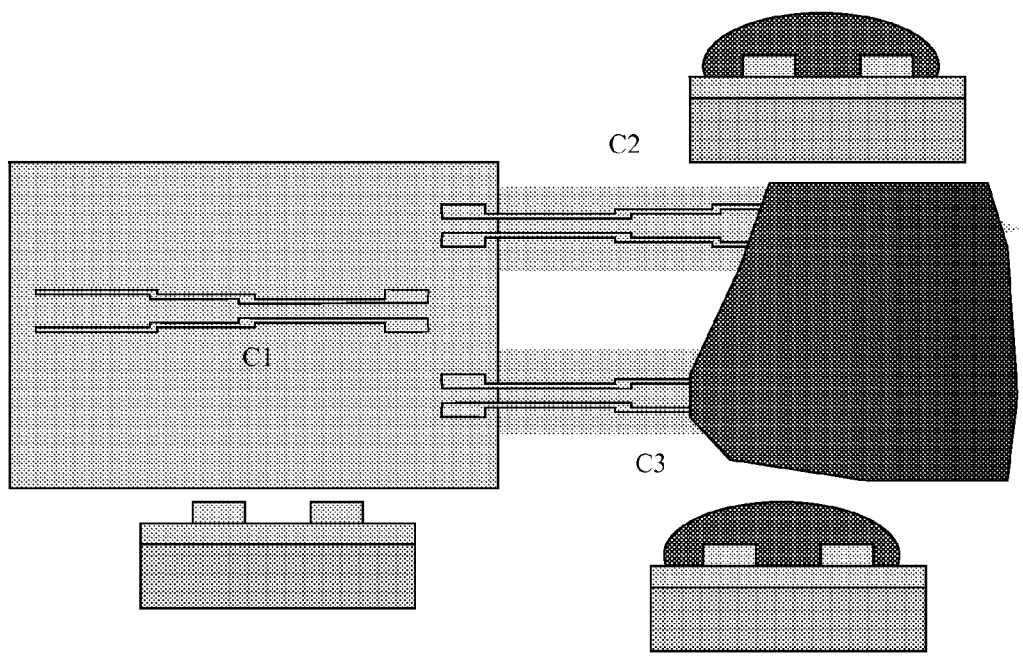

FIGS. 13A-B. A. Another embodiment of the viscosity sensor in which the resonant probe is directly used to puncture skin, extract blood and measure the blood level on the probes, while measuring the viscosity of the blood. B. The capacitors formed by electrodes on the probes can measure the level of the fluid on the probes. Two different probes can measure the meniscus at two different points enabling the measurement of angle of the meniscus. This will enable a way to measure the tilt of the probes with respect to the meniscus for further improving the accuracy of the viscosity measurement.

5. DETAILED DESCRIPTION OF THE INVENTION

For clarity of disclosure, and not by way of limitation, the detailed description of the invention is divided into the subsections set forth below.

5.1. Ultrasonic Viscosity Sensor

An ultrasonic or acoustic viscosity sensor (also referred to herein as a viscometer) is provided that can be used to accurately measure viscosity for fluid samples of less than 1 μl in volume. Methods for measuring viscosity for fluid samples of less than 1 μl in volume are also provided. The viscosity sensor and methods based thereon enable simultaneous measurement of bulk and dynamic (shear-rate dependent) viscosity of a non-Newtonian fluid. The viscosity of any fluid known in the art can be measured. For example, the viscosity of any known bodily fluid, such as blood, pus, mucous, semen, vaginal secretion, saliva or tears, can be indicative of undesired biochemical reactions owing to the presence of disease or foreign agents. In a specific embodiment, the fluid is blood.

Bulk and dynamic viscosity of the non-Newtonian fluid can be measured simultaneously without separating constituents of the fluid, and thus distinguishing the effect of constituents on the viscosity. Dynamic viscosity of the non-Newtonian fluid can be estimated at varying shear rates, to study the deformability of the constituents of the fluid as a function of shear rate. The viscosity sensor can also be tuned to measure viscosity of a non-Newtonian fluid based on the particle size of the fluid's constituents.

In one embodiment, the ultrasonic or acoustic viscosity sensor measures fluid viscosity or fluid flow of a fluid in real time. The viscosity sensor can comprise:

an ultrasonic or acoustic actuator;

at least one microprobe for sensing ultrasound induced motion of the at least one microprobe; and means for generating motion via coupling between the actuator and the at least one microprobe.

Actuator

The viscosity sensor can comprise an ultrasonic or acoustic actuator. In one embodiment, the actuator is driven at its mechanical resonance frequencies.

In another embodiment, the actuator drives at least one microprobe at its mechanical resonance frequency.

In another embodiment, the actuator is a silicon ultrasonic longitudinal mode actuator (FIG. 1) (also referred to herein as a "silicon horn" actuator). Silicon horns and silicon horn actuators are well known in the art, see, e.g., A. Ramkumar, X. Chen and A. Lal, Silicon Ultrasonic Horn Driven Microprobe Viscometer, Proceedings of the International IEEE Ultrasonics Symposium (UFFC 2006), Vancouver, CANADA, October 2006, pp. 1449-1452; Chen, X., Lal, A., Riccio, M., and Gilmour Jr., R., Ultrasonically Actuated Silicon Microprobes for Cardiac Signal Recording, IEEE Transactions on Biomedical Engineering, 53 (8) 2006, p. 1665; Chen, X., Lal, A., Integrated Pressure and Flow Sensor in Silicon-based Ultrasonic Surgical Actuator, IEEE Ultrasonics, Ferroelectrics, and Frequency Control Society Symposium, 2001, Atlanta; Chen, X., Lal, A., Micromachined Ultrasonic Ophthalmic Microsurgical tool with integrated Pressure sensor, Digest of Technical publications, International Conference on Solid State Sensors and Actuators, 2001, Munich, pp. 424-427; Son, I., Lal, A., Hubbard, B., Olsen, T., A multifunctional silicon-based microscale surgical system, Sensors and Actuators A, Volume 91, Issue 3, pp. 351-356, 2000; Lal, A., White, R. M., Silicon microfabricated horns for power ultrasonics, Sensors and Actuators, vol. A54, pp. 542-546, 1996; Amit Lal, Micromachined Silicon Ultrasonic Longitudinal Mode Actuators: Theory and Applications to Surgery, Pumping, and Atomization, Ph.D. Dissertation, University of California, Berkeley, 1996, pp. 1-175; U.S. Pat. No. 5,728,089 to Lal et al., Mar. 17, 1998. Such an actuator can be micromachined using methods known in the art.

The ultrasonic actuator can couple motion to the at least one microprobe through a substrate. Suitable substrates for coupling such motion are known in the art (see, e.g., WO2008/151328 (PCT/US2008/066375; U.S. Pat. No. 5,728,089 to Lal et al., Mar. 17, 1998). The substrate can be made from a semiconducting material. The substrate can comprise both a body portion and the horn portion (also referred to herein as a "catenoid" or catenoid-shaped horn) projecting forward from the body portion. The horn portion can have a blade portion that is free to vibrate.

In another embodiment, silicon ultrasonic longitudinal mode actuator has a varying cross-section for amplifying motion imparted to the at least one microprobe.

In another embodiment, the blade portion can have a forward edge that is significantly thinner than the body portion.

In another embodiment, the actuator imparts mechanical energy to blade portion of the horn. The actuator can be mechanically coupled to the surface (e.g., the top surface) of the body portion.

The viscosity sensor can also comprise piezoelectric elements art (see, e.g., WO2008/151328 (PCT/US2008/066375; U.S. Pat. No. 5,728,089 to Lal et al., Mar. 17, 1998). The ultrasonic actuator can be actuated by piezoelectric elements. In one embodiment, the piezoelectric elements are adhesively attached to the actuator. In another embodiment, the piezoelectric elements are thin piezoelectric films.

Microprobes

The ultrasonic viscosity sensor comprises one or more microprobes. Suitable microprobes for use in the viscosity sensor and the methods disclosed herein are described in WO2008/151328 (PCT/US2008/066375). The design and fabrication of the microprobe can be accomplished using methods of design and fabrication known in the art for other ultrasonic microprobes (see, e.g., WO2008/151328; A. Ramkumar, X. Chen and A. Lal, IEEE Ultrasonics Symposium 2006, pp. 1449-1452, 2006).

In one embodiment, the microprobe is formed from silicon. Other less expensive, mass-produced materials such as stainless steel, nickel, and others known in the art can be used to reduce the cost of making the microprobe. Suitable dimensions for the microprobe can be easily determined by the skilled artisan. In the embodiment shown in FIG. 1, the silicon microprobe 20 is 5 mm long, 100 µm long wide and 140 µm thick projecting outwards at the tip of a silicon horn 10.

The microprobe 20 can comprise a probe body that is formed from silicon. Designs for suitable microprobes for use in the invention are known in the art (see, e.g., WO2008/151328 (PCT/US2008/066375). In one embodiment, the probe body can comprise a core; a lower blade that is integrally formed with the core and that terminates in a lower blade pointed tip extending beyond a distal end of the core; and an upper blade that is formed from silicon nitride deposited on an upper surface of the core opposite the lower blade; terminates in an upper blade pointed tip extending beyond the distal end of the core; and comprises a strain gauge or polysilicon resistor that outputs a signal indicative of strain in the upper blade. The strain gauge can comprise elements etched on the upper blade. The strain gauge can comprise a Wheatstone bridge 250 (for details, see WO2008/151328 (PCT/US2008/066375).

The microprobe can further comprise a base formed from silicon and having a proximal end and a distal end, the probe body extending from the distal end. The base can taper from the proximal end to the distal end. In a preferred embodiment, the base tapers with a catenoid shape. The microprobe can further comprise a second probe body extending from the base (for details, see WO2008/151328 (PCT/US2008/066375).

In one embodiment, the strain gauge or piezoresistor 200 can comprise two sensing resistors 220 so positioned on the probe body as to vary in resistance with strain in the upper blade, and two constant resistors 210 so positioned on the body as not to vary in resistance with strain in the upper blade.

In a specific embodiment, the microprobe defines a channel or tunnel 300 dimensioned for fluid flow (for details, see WO2008/151328 (PCT/US2008/066375).

In one embodiment, the viscosity sensor comprises a single multi-sensor microprobe integrated on the silicon ultrasonic longitudinal mode actuator (silicon horn). In another embodiment, the viscosity sensor can comprise a plurality (e.g., dual) of multi-sensor microprobes integrated on the silicon ultrasonic longitudinal mode actuator (silicon horn). Such an arrangement can increase the sampling of viscosity measurement.

In another embodiment, the multi-sensor microprobe comprises a probe body. In another embodiment, the multi-sensor microprobe comprises two probe bodies extending from the body. In one embodiment, the probe bodies are separated from one another by a distance of preferably no more than 1 mm.

In another embodiment, the multi-sensor microprobe comprises two or more sensors, each of which is coupled to a respective probe body to sense a property of that probe body. Such designs for multi-sensor microprobes are known in the art (for details, see WO2008/151328 (PCT/US2008/066375)). In a specific embodiment, the sensors are a plurality of polysilicon strain gauges or piezoresistors and/or capacitance-based immersion depth sensors.

Single-sensor and multi-sensor microprobes can also comprise, or be functionally connected to, computational circuitry that is responsive to the sensed properties and programmed with instructions to recognize a contact event sensed by one of the probe bodies; to recognize common mode noise sensed by the other of the probe bodies; and output an output signal indicative of the contact event minus the common mode noise (see, e.g., WO2008/151328 (PCT/US2008/066375)). In a specific embodiment, the probe bodies are separated from one another by a distance of no more than 500 µm. The design of such computational circuitry is known in the art In one embodiment, the fluid sample can be ultrasonically driven in the ultrasonic viscosity sensor, e.g., by capillary ultrasonic drive and bubble ultrasonic drive of fluid samples.

The microprobes can be driven by different modalities, e.g., piezoelectrically driven microprobes, ultrasonically driven microprobes (e.g., glass capillaries), or acoustically driven microprobes (e.g., driven by acoustically created bubbles).

Piezoelectrically driven probes can be configured using methods known in the art. Various configurations to couple ultrasonic energy into microprobes, whether directly by integrated piezoelectric or by remote ultrasonic actuators can be used. Piezoresistive readouts can be integrated into the viscosity sensor.

In another embodiment, the viscosity sensor can comprise a piezoelectrically driven glass capillary.

In another embodiment, the viscosity sensor can comprise an optical imager.

In another embodiment, fluid can be bubble-driven in the viscosity sensor. Electrolytically created, but acoustically driven microbubbles in samples can be used to measure viscosity.

In another embodiment, the viscosity sensor can comprise a multi-sensor microprobe. The microprobe can comprise, for example, one or more strain gauges and/or immersion depth capacitance sensors. In other embodiments, the viscosity sensor comprises a single sensor microprobe.

5.2. Operation of the Viscosity Sensor

In another embodiment, the viscosity sensor operates in acoustic frequencies between 10 Hz to 20 kHz.

In another embodiment, the viscosity sensor operates in mid ultrasonic frequencies between 20 kHz to 500 kHz.

In another embodiment, the viscosity sensor operates in upper ultrasonic frequencies between 500 kHz to 10 MHz.

In another embodiment, the viscosity sensor generates high amplitude (e.g., 1-10 µm motion in the fluid of interest.

In certain embodiments, the ultrasonic or acoustic viscosity sensor can be used to measure viscosity in small volumes of a fluid of interest, e.g., less than 1 µl. In other embodiments, the sensor can measure viscosity in sample volumes that are 1-10 µl, 10-20 µl, 20-30 µl, 30-40 µl, 40-50 µl, 50-60 µl, 60-70 µl, 70-80 µl, 80-90 µl or 90-100 µl or greater than 100 µl.

In a specific embodiment, the viscosity sensor uses a low sample volume. In one embodiment, the dimensions of the microprobe can accommodate sample volumes 1 µl or lower. This sample size corresponds, for example, to a blood sample associated with diabetes in-home sugar testing equipment.

In one embodiment, the ultrasonic or acoustic viscosity sensor is a mid-frequency (30-50 kHz) resonant viscosity sensor.

In another embodiment, the sensor generates high amplitude motion that is 1 µm or greater.

The sensor generates the high amplitude (>1 µm) motion via nonlinear coupling between longitudinal to transverse motion to measure fluid viscosity.

Vibrations are induced by the λ/2 longitudinal resonance of the ultrasonic longitudinal mode actuator (silicon horn). Since shear (non-linear vibration) and bulk (silicon horn's λ/2 longitudinal resonance) damping can be observed at two different frequencies, the viscosity sensor can simultaneously measure the static (bulk) and dynamic (shear-rate dependent) viscosity of a fluid (FIG. 1, bottom diagram).

In another embodiment, the ultrasonic actuator can be a remote ultrasonic actuator.

FIG. 1 shows a specific embodiment of the viscosity sensor. FIG. 1, top left is a photograph of the viscosity sensor. Piezoresistors 200 (in this embodiment, ~9 kΩ) are located at the junction of an actuator (in this embodiment, a catenoid silicon horn) and a pair of microprobes to sense ultrasound-induced strain oscillations. PZT plates (piezoresistive transducer plates). In the embodiment shown in FIG. 1, four polyresistors 200, consisting of two constant polyresistors 210 and two sense polyresistors 220 are connected in a Wheatstone bridge 250 configuration.

Furthermore, since fluid viscosity is a strong function of probe insertion depth, the viscosity sensor can comprise means for measuring and/or calibrating immersion depth. Such means can be used for self-calibration of the viscosity sensor. In one embodiment, the means for measuring immersion depth is based on measurement of capacitance between two electrodes.

In a specific embodiment, the means for measuring immersion depth are capacitance-based immersion depth sensors that can be used for self-calibration of the viscosity sensor, i.e., for calibrating a viscosity measurement. The viscosity sensor thus can measure the vibration damping at varying microprobe immersion depths.

The capacitance-based immersion depth sensor can comprise distance-coding capacitance. In another embodiment, the distance-coding capacitance is formed by at least two metal traces on the capacitance-based immersion depth sensor. In another embodiment, the capacitance is measured as a function of frequency to extract the dielectric constant of the fluid as a function of frequency.

In one embodiment, immersion depth calibration is implemented by measuring the capacitance at discrete steps (FIG. 1), which provide distinct motion artifacts from velocity and depth measurement. FIG. 1, bottom, is a diagram showing the microprobes being used for multi-sensing viscosity (bulk and shear) measurements in microdroplet fluid sample. The multi-sensing measurements can be conducted at specific or desired immersion depths. The diagram depicts simultaneous detection of shear-based viscosity $f_1$ and bulk viscosity at $f_2$ in low sample volumes because of vibration wavelengths being much smaller than droplet diameter.

For example, the device can comprise means for distance-coding of a capacitance measurement. In one embodiment, means for distance-coding of capacitance can comprise a plurality of platinum traces (e.g., 10 μm wide and 0.2 μm thick) positioned on the device. Such means can be, in certain embodiments, co-fabricated on the microprobes.

FIG. 3 shows the linear dependence of the capacitance signal with increasing depth of immersion of the microprobes in the liquid FIG. 1, top right, shows metal traces (in this embodiment, 10 μm×0.2 μm platinum traces) that are located at discrete steps along the microprobes that serve as capacitance-based probe immersion depth sensors. The spacing of the sensors can be readily determined by the skilled artisan.

The ultrasonic or acoustic viscosity sensor can comprise means for measuring damping of the mechanical vibrations of the at least one microprobe in the fluid of interest.

In one embodiment, the means for measuring damping of the mechanical vibrations comprises at least two piezoresistors or strain gauges located at the junction of the silicon horn and the microprobes, wherein at least one of the piezoresistors measures the amplitude of motion of the at least one microprobe and wherein at least one of the piezoresistors measures the motion of the actuator.

The resistance of the piezoresistor or strain gauge changes with the strain experienced. In one embodiment, the piezoresistor or strain gauge has a nominal resistance of about 10 kΩ. In other embodiments, the piezoresistor or strain gauge has a nominal resistance of 1-5, 5-10, 10-15 or 15-20 or 20-50 kΩ. Other suitable resistances can be easily determined by the skilled artisan.

Figure 2:
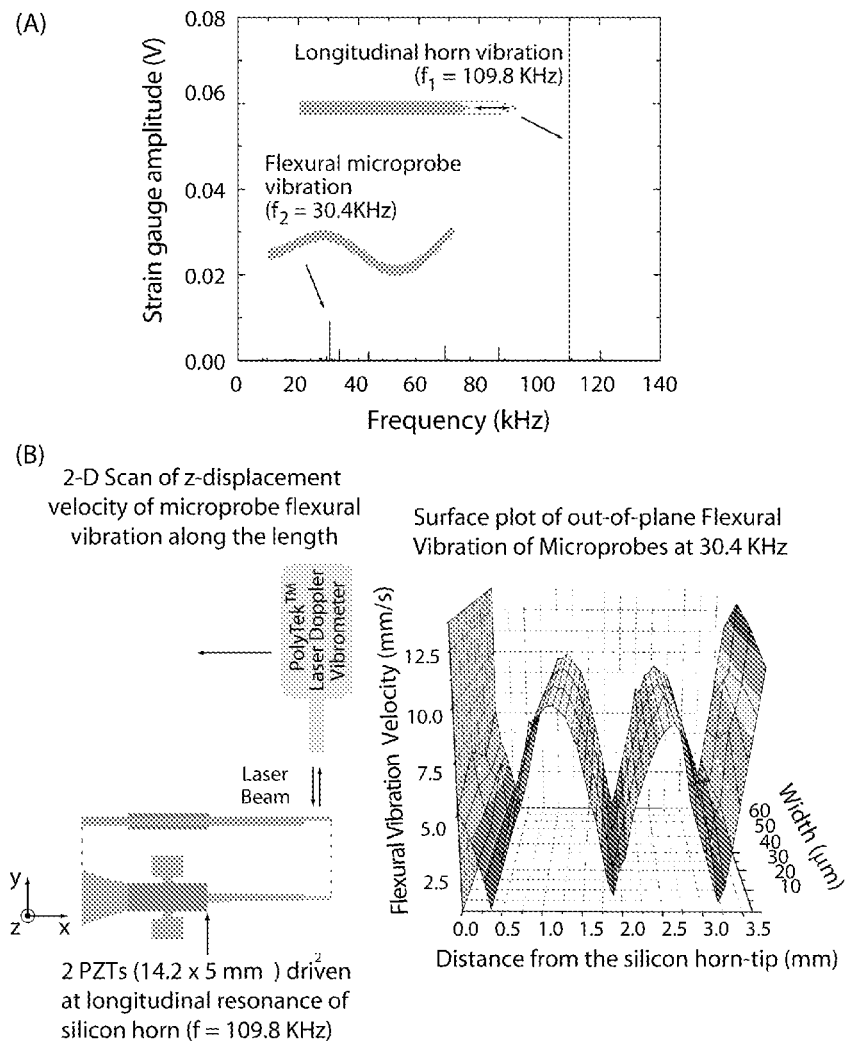

The piezoresistor or strain gauge can be integrated at the junction of the actuator and the microprobe to measure longitudinal and flexural oscillating motion (see FIGS. 1 and 2). In a specific embodiment, the strain gauge is a polysilicon strain gauge or polysilicon resistor (polyresistor) (FIG. 1).

In another embodiment, the resistors or strain gauges are connected in a Wheatstone bridge 250 configuration (FIG. 1, see, e.g., A. Ramkumar, X. Chen and A. Lal, IEEE Ultrasonics Symposium 2006, pp. 1449-1452, 2006).

The silicon horn actuator can be actuated at its λ/2 longitudinal resonance, which exerts longitudinal strain at the tip of the horn and induces a parametrically excited flexural vibration mode in the microprobe. The magnitude of signal corresponding to both the oscillation frequencies can be measured from the Fast-Fourier Transform (FFT) of the amplified Wheatstone bridge voltage.

FIGS. 2A-B show a two-dimensional (2D) laser Doppler vibrometer scan of silicon horn actuator-based microprobes that indicates a mode with three displacement nodes.

In specific embodiments, mid- or high-frequency resonant ultrasonic viscosity sensors for measuring fluid viscosity or flow are provided (FIG. 1). The mid- or high-frequency resonant ultrasonic viscosity sensor can comprise:

a silicon horn 10; and a multi-sensor microprobe 20 for sensing ultrasound induced strain oscillations, wherein:

the multi-sensor multiprobe comprises:

at least one strain gauge (e.g. polysilicon strain gauge) or piezoresistor 200 connected in a Wheatstone bridge 250 configuration, and a capacitance-based immersion depth sensor 230, and the sensor generates high amplitude motion via nonlinear coupling between longitudinal to transverse motion.

In one embodiment, the viscosity sensor is mid-frequency resonant and the mid-frequency is 20-500 kHz.

In another embodiment, the viscosity sensor is high-frequency resonant and wherein the high-frequency is 500 kHz-10 MHz.

5.3. Methods for Measuring Fluid Viscosity Using the Ultrasonic Viscosity Sensor Methods for measuring fluid viscosity are also provided. In one embodiment, the method can comprise the steps of providing an ultrasonic viscosity sensor and monitoring viscous damping of non-linear flexural vibrations of microprobes on the viscosity sensor.

In one embodiment, the method for measuring fluid viscosity or fluid flow of a fluid of interest comprising the steps of:

providing an ultrasonic viscosity sensor as described herein; and measuring viscous damping of non-linear flexural vibrations of the microprobe induced by the λ/2 longitudinal resonance of the silicon horn.

In one embodiment, non-linear flexural vibrations of the microprobe can comprise longitudinal and flexural oscillating motions.

In another embodiment, the step of measuring viscous damping comprises measuring viscous damping at multiple frequencies. In another embodiment, a first of the multiple frequencies is the actuator longitudinal mode frequency and a second of the multiple frequencies is the microprobe resonance frequency.

In another embodiment, the step of measuring viscous damping can comprise measuring shear (non-linear vibration) damping and bulk (silicon horn's λ/2 longitudinal resonance) damping at two different frequencies, thereby simultaneously measuring the static (bulk) viscosity and dynamic (shear-rate dependent) viscosity of the fluid of interest.

In another embodiment, the method can comprise the step of calculating the frequency and magnitude of a signal corresponding to the multi-frequency excitation from the Fast Fourier Transform (FFT) of the amplified Wheatstone bridge voltage signal corresponding to the motion of a cantilever of the microprobe.

In another embodiment, the method can comprise the step of calibrating immersion depth. In one embodiment, the calibrating step can comprise measuring capacitance at discrete steps.

As mentioned above, the method comprises measuring viscous damping of non-linear flexural vibrations of the microprobe induced by the λ/2 longitudinal resonance of the silicon horn. Damping of the microprobe occurs because the liquid on the surface of the microprobe is viscously entrained with the shear acoustic wave penetrating only a small distance into the fluid sample. This decay length (δ) is given by $$\delta = \left(\frac{2\eta}{\omega\rho}\right)^{\frac{1}{2}}$$

(I. Etchart, H. Chen, P. Dryden, J. Jundt, C. Harrison, K. Hsu, F. Marty, B. Mercier, "MEMS sensor for density-viscosity sensing in a low-flow microfluidic environment", *Sensors and Actuators A.*, vol. 141, pp. 266-275, 2008), where η and ρ are the fluid viscosity and density, respectively, and ω=2πf is the angular frequency of flexural vibration of the microprobe(s).

The viscosity of the fluid of interest can be estimated at different shear rates by varying the piezoelectric transducer (PZT) actuation voltage. In one embodiment, the viscosity of the fluid of interest is used to assess coagulation time. In another embodiment, the coagulation progression of the fluid of interest is measured. In a specific embodiment, the coagulation progression of blood is measured.

For example, to perform such a calculation for blood viscosity, based on known normal blood plasma, ρ=1060 Kg/m³ and η=0.001 Poise, the maximum decay length will be $\delta_0$~2.1 μm at the silicon horn's λ/2 longitudinal resonance (109.8 KHz). This length is much smaller than the dimensions of the red blood cells (RBCs), which are on the order of 8 μm in length. Unless the cells are very close the surface of the microprobes, the mechanical movement that entrains the fluid will not perturb the RBCs, thus, the microprobe only "sees" the plasma surrounding the cells and measures plasma properties (K. K. Kanazawa, J. G. Gordon, "Frequency of a quartz microbalance in contact with liquid", *Anal. Chem.*, vol. 57, no. 8, pp. 1770-1771, 1985). The advantage of this approach is that it allows the extraction of information on plasma viscosity without having to separate the plasma from the whole blood.

The frequency of lower parametric flexural vibrations manifested in the microprobes can be adjusted so that the decay length is greater than 8 μm, thus allowing for whole blood viscosity measurement with the effect of RBCs. By measuring both whole blood and plasma viscosity simultaneously, the effect of RBCs can be precisely determined. Also, in embodiments in which the viscosity sensor is calibrated for different immersion depths, the viscosity of a fluid such as blood can be estimated at different shear rates by varying the piezoelectric transducer (PZT) actuation voltage. It will be apparent to the skilled artisan that the above-described approach can be used to extract information about the viscosity of other fluids of interest.

5.4. Uses for the Viscosity Sensor

The viscosity of any fluid of interest can be measured using the viscosity sensor and methods based thereon.

In certain embodiments, the sensor can be used in clinical and home-use devices that utilize viscosity data about fluids, e.g., body fluids.

In one embodiment, the viscosity sensor is re-usable. For example, the device can be cleaned in bleach after every measurement and re-used in the clinical diagnostic setting for maximal use of each sensor.

In another embodiment, several assays on different samples can be performed simultaneously. For example, a glass capillary could also be used to set up groups of data performing different assays simultaneously.

In another embodiment, the viscosity sensor can be integrated as a component into a hand-held reader, e.g., a reader for blood-glucose measurements.

In another embodiment, the viscosity sensor can comprise a plastic packaged capillary wick into which the fluid sample is introduced or driven. The fluid sample can then be pumped into a MEMS sensor of any suitable type known in the art.

In certain embodiments, the viscosity sensor is used in clinical settings as a probe can be easily inserted in microliters of sample collected from patients, such as a drop of blood. In one embodiment, the viscosity sensor is integrated into a strip format. In a specific embodiment, the strip format is a blood-glucose measurement strip.

The device can be scaled to very small scales so that it can be incorporated within existing blood-sensing strips, for easy dissemination to millions of patients who already use blood-sugar strips.

In a specific embodiment, the viscosity sensor is used to perform a Prothrombin Time (PT) test. The PT test is an important index for the activity of coagulation factors of the extrinsic pathway; it is the coagulation time when tissue thromboplastin (a tissue factor) and calcium ion are added into the plasma specimen to induce coagulation formation (H. L. Bandey, R. W. Cemosek, W. E. Lee III, L. E. Ondrovic, "Blood rheological characterization using the thickness-shear mode resonator", *Biosensors and Bioelectronics*, vol. 19, pp. 1657-1665, 2004).

In another embodiment, the viscosity sensor is used to perform a Partial Thromboplastin Time (PTT) test. The PTT test is an indicator of coagulation factors of the intrinsic pathway, measuring the time whole blood takes to coagulate. PTT is often used as a starting place when investigating the cause of a bleeding or thrombotic episode. The PTT test is also used to monitor these therapies. It does not directly measure the anticoagulants used but measures their effect on blood clotting.

Since the viscosity sensor is capable of measuring plasma viscosity and blood viscosity simultaneously, the viscosity sensor can perform the PT and PTT coagulation tests simultaneously, thus allowing for standardized results for both tests under the same conditions, giving the doctor entire information about the blood coagulation cascade.

In another embodiment of the viscosity sensor, shown in FIGS. 13A-B, the microprobe is used directly to puncture skin, extract blood and measure the blood level on the probes, while measuring the viscosity of the blood (FIG. 13A). The capacitors formed by electrodes on the probes can measure the level of the fluid on the probes (FIG. 13B). Two different probes can measure the meniscus at two different points enabling the measurement of angle of the meniscus. This enables a way to measure the tilt of the probes with respect to the meniscus for further improving the accuracy of the viscosity measurement.

The following examples are offered by way of illustration and not by way of limitation.

6. EXAMPLES

Example 1: Viscosity Measurement of Blood Samples

Introduction

This example demonstrates the development of a viscosity sensor that can be used to accurately measure viscosity for less than 1 μl of blood sample, so that clinical and home-use devices that utilize viscosity data can be realized. The device can be integrated into a typical strip test, much like those used for blood-glucose measurement (FIG. 7).

Medical diagnosis of disease often requires the viscosity of body fluids, most importantly that of blood (R. S. Rosenson, A. McCormick, E. F. Uretz, "Distribution of blood viscosity values and biochemical correlates in healthy adults," Clin. Chem., vol. 42, no. 8, pp. 1189-1195, 1996). Blood rheology in vivo can be used for prediction of blood flow through capillaries of varying sizes, while its in vitro rheology can be used for diagnosis and monitoring of diseases. Also, changes in blood rheology have been seen to contribute to or aggravate cardiovascular disorders such as myocardial infarction and hypertension (S. Chien, "Blood rheology in myocardial infarction and hypertension," Biorheology, vol. 23, no. 6, pp. 633-653. 1986; T. Somer, H. J. Meiselman, "Disorders of Blood Viscosity," Annals of Medicine, vol. 25, pp. 31-39, 1993). Clinical hemorheological tests measure the red blood cell (RBC or erythrocyte) aggregation by the erythrocyte sedimentation rate (ESR) and the plasma viscosity. Physiological conditions leading to alternation of plasma proteins (such as fibrinogen) results in a change in the ESR and plasma viscosity. Correlation to blood rheology can be used as a good indicator for prognosis, diagnosis and/or monitoring disease processes such as cancer, cardiovascular disease, etc. For example, inflammatory biomarkers (fibrinogen) and plasma viscosity have been observed to be significantly associated with death due to myocardial infarction or coronary heart disease (S. G. Wanamethee, P. H. Whincup, A. G. Shaper, A. Rumley, L. Lennon, G. D. O. Lowe, "Circulating inflammatory and hemostatic biomarkers are associated with risk of myocardial infarction and coronary death, but not angina pectoris, in older men," J. Thromb. Haemost, vol. 7, pp. 1605-1611, 2009). Incidence of type 2-Diabetes has been shown to be strongly related to high whole blood viscosity (WBV) (L. J. Tamariz, J. H. Young, J. S. Pankow, H.-C. Yeh, M. I. Schmidt, B. Astor, F. L. Brancati, "Blood Viscosity and Hematocrit as Risk Factors for Type 2 Diabetes Mellitus The Atherosclerosis Risk in Communities (ARIC) Study," Am J. Epidemiol., vol. 168, no. 10, pp. 1153-1160, 2008), thus allowing a measure of blood viscosity to be a prognosis tool. Also, monitoring plasma viscosity can help in the prediction and diagnosis of plasma hyperviscosity syndrome and sickle cell disease (T. Somer, H. J. Meiselman, "Disorders of Blood Viscosity," Annals of Medicine, vol. 25, pp. 31-39, 1993). Additionally, a measure of blood viscosity can help in monitoring interventions to alter blood viscosity such as diet, alcohol, pharmaceuticals etc.

FIG. 8 shows the currently used hemorheological tests for diagnosis and monitoring of diseases are blood coagulation tests namely, Prothrombin Time (PT) and Partial Thromboplastic Therapy (PTT). The Prothrombin Time (PT) test is an important index for the activity of coagulation factors of the extrinsic pathway—it is the coagulation time when tissue thromboplastin (a tissue factor) and calcium ion are added into the plasma specimen to induce coagulation formation. Warfarin and Coumarin are prescribed to slow down the extrinsic pathway and the effectiveness is measured by the PT test.

The Partial Thromboplastin Time (PTT) test is an indicator of coagulation factors of the intrinsic pathway, measuring the time whole blood takes to coagulate. PTT is often used as a starting place when investigating the cause of a bleeding or thrombotic episode. The PTT test is used to determine the effectiveness of oral anti-coagulation therapy (e.g. Heparin) prescribed to patients with perturbations in the intrinsic pathway. The above coagulation tests do not directly measure the effectiveness of drugs (Warfarin, Coumarin, Heparin etc.) used on blood viscosity (i.e. thinning or reducing blood viscosity) but measures their second order effect i.e. blood clotting. The tests conducted in clinics require large samples of blood (3-5 ml) requiring the addition of anti-coagulants, with high turn-around times of 1-2 hours. The currently existing hand-held point of care units for home coagulation monitoring (COAGUCHEK®, HEMOSENSE® etc.), follow the pin-prick blood sampling and strip method as in the blood-glucose meters, and measure blood coagulation times (PT and PTT). Though these devices are portable and easy to use, they are expensive (upwards of $1500/unit and ~$4/strip) and do not measure the effect of the anti-coagulation therapy on the actual physical quantity of blood being affected, i.e. the whole blood viscosity. A real-time measurement of the physical property of the complex fluid (here, blood viscosity) can help give a real-time feedback on the effectiveness and response time of the treatment/therapy in a clinic allowing for tighter control. Such a device could in effect be used for measuring standardized PT and PTT coagulation times for home monitoring as well, thus giving a complete picture of the therapy induced changes to blood.

Whole Blood and Plasma Viscosity Measurement

Red blood cells (RBCs), which compose about 35-40% of the volume of mammalian blood, are known to be deformable and contribute to the non-Newtonian nature of blood, i.e., its viscoelastic behavior (D. R. Gross, N. H. Hwang, "The Rheology of Blood, Blood Vessels and Associated Tissues," Sitjthoff and Noordhoff, Rockville, Md., 1981). Whole blood viscosity (WBV) is observed to have shear-rate dependence due to the deformability of the RBCs. This has been shown to have a strong correlation to hypertension (R. B. Devereux, D. B. Case, M. H. Alderman, T. G. Pickering, S. Chien, J. H. Laragh, "Possible Role of Increased Blood Viscosity in the Hemodynamics of Systemic Hypertension," Am. J. Cardiol., vol. 85, pp. 1265-1268, 2000). Also, since the blood volumes available from patients are small, they must be analyzed quickly preferably without the addition of anticoagulants. The currently existing methods for clinical diagnosis and in vitro study of blood in laboratories, involve the addition of anti-coagulants thus deviating from the true physiological state of blood (W. I. Rosenblum, "In vitro measurements of the effects of anticoagulants on the flow properties of blood: The relationship of these effects to red cell shrinkage," Blood, vol. 31, no. 2, pp. 234-241, 1968). The plasma viscosity of blood also measured in clinical laboratories requires the separation of RBCs from blood, requiring post-processing of blood and delayed response times. Also, the instruments being bulky pose a practical difficulty in order to have whole blood and plasma viscosity as a point-of-care measurement for rapid on-site diagnosis. There is a current need for low-sample volume (<1 µl), rapid real-time measurement of rheological properties of whole blood and plasma (viscosity and coagulation) in vitro or in vivo. Such an instrument, together with biosensors such as glucose measurement for diabetic patients, could serve as an invaluable tool for rapid diagnosis and monitoring of disease and blood function.

Acoustic wave sensors (piezoelectric crystals and electroceramics) have been used extensively in the measurement of fluid viscosity (H. Muramatsu, M. Suda, T. Ataka, A. Seki, E. Tamiya, I. Karube, "Piezoelectric resonator as a chemical and biochemical sensing device," Sens. Act., vol. 21A, no. 1-3, pp. 362-368, 1990; S. J. Martin, A. J. Ricco, and R. C. Hughes, "Acoustic wave devices for sensing in liquids," 4th International Conference on Solid-State Sensors and Actuators (Transducers'87), Tokyo, Japan, pp. 478-481, June 1987; B. A. Martin, S. W. Wenzel, and R. M. White, "Viscosity and density sensing with ultrasonic plate waves," Sens. Act., vol. 22A, no. 1-3, pp. 704-708, 1990). The physical properties of the fluid can be extracted from the change in resonant frequency, quality factor and the magnitude of vibration of a resonator. Thickness-shear mode (TSM) resonators have been reported to be used in blood rheological characterization such as viscosity and coagulation measurement. Since the acoustic shear wave thickness in the blood in contact with the TSM (high frequency) resonators is much smaller than the size of a RBC, only plasma viscosity can be measured and the effect of RBCs is not sensed (H. L. Bandey, R. W. Cernosek, W. E. Lee III, L. E. Ondrovic, "Blood rheological characterization using the thickness-shear mode resonator", Biosens. and Bioelec., vol. 19, pp. 1657-1665, 2004; T.-J. Cheng, H.-C. Chang, T.-M. Lin, "A piezoelectric quartz crystal sensor for the determination of coagulation time in plasma and whole blood", Biosens. and Bioelec., vol. 13, no. 2, pp. 147-156, 1998). At the opposite extreme are low frequency resonant devices with high shear wave thickness that can become bulky, with the size approaching that of commercial tabletop viscometers. A mid-frequency (30-100 kHz) resonant viscosity sensor is provided that generates high amplitude motion (>1-micron) via nonlinear coupling between a longitudinal to transverse motion to measure fluid viscosity with a self-calibrating immersion depth sensor. This instrument is likely to be clinically suitable, as a probe that can be easily inserted in microliters of sample collected from patients, such as a drop of blood (FIGS. 1, 7). It has been demonstrated previously (A. Ramkumar, X. Chen A. Lal, "Silicon Ultrasonic Horn Driven Microprobe Viscometer," IEEE Ultrasonics Symposium 2006, pp. 1449-1452, 2006) that a high-amplitude horn-shaped longitudinal mode resonator's quality factor is sensitive to fluid viscosity into which the probes are inserted. However, this capability is limited as it is not easy to measure how much of the probe is inserted into the fluid and, the shear-rate dependent fluid viscosity cannot be distinguished. Here fluid viscosity measurement is accomplished by monitoring the viscous damping of nonlinear flexural vibrations of the microprobes, induced by the $\lambda/2$ longitudinal resonance of silicon horn actuators. Real-time coagulation in a rat-blood droplet (~5 µl) as a function of time is measured by monitoring the resonance frequency of the flexural vibration. This demonstrates the sensor's applicability as a rapid blood coagulation sensor alongside measuring whole blood viscosity. Furthermore, since the viscosity is a strong function of probe insertion depth, capacitance-based immersion depth sensors have been integrated into the viscosity sensor for self-calibration of probe depth, or fluid immersion, of the ultrasonic viscosity sensor.

Design and Fabrication of Viscosity Sensor

The design and fabrication of the microprobe is similar to the ultrasonic microprobes reported earlier (A. Ramkumar, X. Chen A. Lal, "Silicon Ultrasonic Horn Driven Microprobe Viscometer," IEEE Ultrasonics Symposium 2006, pp. 1449-1452, 2006). In the embodiment described in the present example, the silicon microprobes are 4 mm long, 100 µm wide and 140 µm thick projecting outwards at the tip of the horn (FIG. 1). The polysilicon strain gauges and immersion depth capacitance sensor have been integrated to form a multi-sensor microprobe. Dual multi-sensor microprobes are integrated on the actuator (silicon horn) to increase the sampling of viscosity measurement but the measurement can be performed by using a single microprobe. Polysilicon strain gauges (~10 kΩ) are connected in a Wheatstone bridge 250 configuration, are integrated at the junction of the horn and the microprobe to measure the longitudinal and flexural oscillating motion (FIGS. 1, 2). The silicon horn actuated at its $\lambda/2$ longitudinal resonance (109.8 kHz) exerts longitudinal strain at the tip of the horn, and induces a non-linear flexural vibration mode (30.4 kHz) in the microprobes. From the Fast-Fourier Transform (FFT) of the amplified Wheatstone bridge voltage, the magnitude of vibration corresponding to both the oscillation frequencies is measured (FIG. 2A). A 2D laser Doppler vibrometer scan of microprobes indicates a mode with three displacement nodes with $\lambda$~2.83 mm (FIG. 2B). Immersion depth calibration is implemented by measuring the capacitance at discrete steps, which provide distinct motion artifacts as the liquid with the much higher dielectric constant surrounds the traces. The distance coding capacitance is formed by platinum traces (10 µm wide and 0.2 µm thick) co-fabricated on the microprobes (FIG. 1). FIG. 3 shows the linear dependence of the capacitance signal with increasing depth of immersion of the microprobes in saline solution (sensitivity=4.3 nF/mm).

Results

Ethylene Glycol Viscosity Measurement

The flexural vibration amplitude was monitored as the microprobes were immersed in ethylene glycol at different immersion depths and was observed at increasing piezoelectric transducer (PZT) actuation voltages (1-10 $V_{pp}$). With increasing immersion depth of microprobes in deionized water, the damping is observed to increase with increasing contact with fluid (FIG. 4). FIG. 5 shows the decrease in vibration amplitude at $8V_{pp}$ PZT actuation as the microprobe is immersed in solutions of varying viscosities. As a first approximation, the viscous fluid damping of the microprobe is modeled by assuming the immersed part of the vibrating probe to be an oscillating sphere immersed in a liquid (C. Riesch, E. K. Reichel, F. Keplinger and B. Jakoby, Journal of Sensors, Article ID 697062, 2008), and the damping model was shown to agree reasonably with the data in FIG. 5.

The parameters in the model are dependent of the microprobe mass and geometry, and the immersion depth. Therefore, a wide range of viscosities can be accurately measured by monitoring the amplitude of the vibration in the viscosity sensor at different immersion depths (in this embodiment, both capabilities are integrated on the device).

The performance of the viscosity sensor can be assessed by calibrating it using a standard, such as ethylene glycol, with a known viscosity at a given temperature. The quality of the analytical damping model's fit to data obtained from the viscosity sensor can be used to assess its performance. Fluid viscosity can also be determined by monitoring the change in frequency ($f_0$) and quality factor ($f_0/\Delta f$) of the flexural and longitudinal vibrations. This can permit higher sensitivity when measuring fluid viscosity.

Measurement of Rat Whole Blood Coagulation

The viscosity sensor was used to measure rat whole blood coagulation. Whole blood was obtained from a Sprague-Dawley rat (44 weeks old) using exsanguination. No anticoagulants were added. The flexural vibration frequency was monitored as the microprobe of the viscosity sensor was immersed in the blood at a depth of ~1 mm. Initially, the red blood cells (RBCs) coated the microprobe, lying within the shear thickness and thus loading the vibration by reducing its frequency (Phase I, FIG. 6). The blood coagulation cycle ramped up by the formation of blood clots (coagulated RBCs) with sizes bigger than the shear thickness, and thus reducing the loading on the vibration frequency (Phase II, FIG. 6). Finally, the blood coagulation cycle ended at ~430 seconds (Phase III, FIG. 6), which was close to that known in the art (T.-J. Cheng, H.-C. Chang, T.-M. Lin, "A piezoelectric quartz crystal sensor for the determination of coagulation time in plasma and whole blood", Biosensors and Bioelectronics, vol. 13, no. 2, pp. 147-156, 1998). The residual damping observed at the end of the coagulation cycle was mostly due to the plasma; few RBCs and the fibrous network of clots formed. The microprobe was cleaned afterwards by immersing in diluted bleach solution and actuating the PZT at $20V_{pp}$, and the frequency and amplitude of vibration returned to the baseline values.

These experiments demonstrate that fluid viscosity can be measured by monitoring the flexural vibration of the immersed microprobes, with precise control of the depth of immersion. Since the acoustic shear thickness of the flexural vibration is close to the size of a RBC (C. Riesch, E. K. Reichel, F. Keplinger, B. Jakoby, "Characterizing Vibrating Cantilevers for Liquid Viscosity and Density Sensing," J. Sensors, Article ID 697062, pp. 1-9, 2008), the viscous damping was influenced by the RBCs, thus enabling the measurement of whole blood viscosity. Also, by varying the PZT actuation voltage the microprobe flexural vibration rate can be varied, and hence shear rate dependence of whole blood viscosity can be measured. In addition, the damping in the silicon horn's longitudinal vibration (109.8 kHz) having a shear thickness much smaller than the size of a RBC will allow for measurement of blood plasma viscosity (A. Ramkumar, X. Chen A. Lal, "Silicon Ultrasonic Horn Driven Microprobe Viscometer," IEEE Ultrasonics Symposium 2006, pp. 1449-1452, 2006). Since the shear (non-linear vibration) and bulk (silicon horn's λ/2 longitudinal resonance) damping can be observed at two different frequencies, one can simultaneously measure the plasma (bulk) and whole (shear-rate dependent) blood viscosity in low-sample volumes (~1-3 μl). In addition, the natural and drug-induced blood coagulation cascade can be precisely monitored as a function of time. Circuitry can be designed using methods known in the art to monitor the change in frequency $f_0$ and quality factor ($f_0/\Delta f$) of the flexural and longitudinal vibrations of the microprobes when immersed in a fluid. This enables higher sensitivity when measuring fluid viscosity.

Example 2: Assessment of Flow Measurement Ability of Piezoresistive Microprobes

This example describes an experiment that tested the flow-sensing properties of an embodiment of the device. This embodiment of the device comprised piezoresistive microprobes 20 that were positioned upside down and perpendicular into a narrow channel 300 that was approximately 8 mm width and approximately 5 cm in length. The probe tips extended approximately 2 mm inside the channel. FIG. 9a shows a photograph of this embodiment of the device. FIG. 9b shows the tips of the piezoresistive probes inside the tunnel (channel) 300.

Water was conducted through a narrow (~1 mm in diameter) tubule 400 inside the channel. The other side of tubule was connected to a 30 ml syringe while sitting in a syringe driver 600. The driver pushed the syringe to produce a 30 ml/min flow of water. The probes were connected to an interface to monitor the induced voltage in the Wheatstone bridge 250 integrated into the bodies of the microprobes. Such an interface is commonly known in the art. A 5 kHz signal was used in this interface for data sampling for period of 20 sec.

When the syringe driver started to pump water into channel, it took some time for the system to become stable. Voltage changes were parabolic in this regime. In addition, the measured voltage was constant or linear depending on the water depth in channel. If the water filled the channel gradually during the experiment, a linear regime in measured voltage was observed. If the channel saturated from water and became almost constant in depth, the voltage became constant during the measurements.

FIG. 10 shows the measured voltage versus time in probes when the channel was being filled. The syringe driver was turned on and sampling started. It took about 3.5 seconds for the system to stabilize and then a linear regime started. In this experiment, the slope of the linear regime was 5.9 mv/sec.

Another measurement was then done after a 5-second pause after switching the syringe driver on to monitor the stable condition of the system. FIG. 11 plots voltage versus time in this experiment. In the case of constant channel depth, the same method can be used to measure probe voltage.

As shown in FIG. 12, it takes around 3.5 seconds for system to become stable, then voltage become constant; then voltage immediately drops to its initial value ($-1.88^V$). The plot is not uniformly constant; vibration noise in the environment, e.g., syringe driver is a potential noise source. Second, due to small channel length, water hits the holder wall and bounce back thereafter and this could cause a voltage drop. Finally, any turbulence in channel could cause a drop at output voltage. The average voltage during the experiment was $-1.835^V$ and voltage drop owing to fluid flow (30 ml/min) was 45 mV (FIG. 12).

By making a longer channel to decrease settling time of system, the performance of the system can be improved. Additional measurements in different flow values can be used to determine a suitable range of flow measurement for fabricated piezo-resonators. Performing measurements with the device positioned on a noise cancellation table can be used to obtain more constant voltages.

The present invention is not to be limited in scope by the specific embodiments described herein. Indeed, various modifications and variations of the invention in addition to those described herein will become apparent to those skilled in the art from the foregoing description and can be made to the invention without departing from the spirit and scope of the invention. Thus, it is intended that the present invention cover the modifications and variations of this invention provided they come within the scope of the appended claims and their equivalents.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. An ultrasonic viscosity sensor having a microprobe with patterned electrodes for determining a viscosity of a fluid comprising:
   an ultrasonic actuator for producing ultrasonic waves;
   a microprobe for coupling the ultrasonic waves to the fluid, wherein at least an amplitude of the ultrasonic waves at the microprobe determines the viscosity of the fluid, and wherein the microprobe includes patterned electrodes for determining an immersion depth of the microprobe in the fluid from a capacitance between conductive traces on the patterned electrodes,
   wherein the ultrasonic viscosity sensor determines a shear decay length ($\delta$) at an actuator resonance, wherein $\delta$ is determined by at least the viscosity of the fluid, a density of the fluid, and a frequency of the ultrasonic waves.

2. The ultrasonic viscosity sensor of claim 1, further comprising: a substrate.

3. The ultrasonic viscosity sensor of claim 2, wherein the ultrasonic actuator produces longitudinal ultrasonic waves coupled through the substrate to the fluid, wherein the longitudinal ultrasonic waves include ultrasonic motion along a length of the microprobe.

4. The ultrasonic viscosity sensor of claim 1, wherein the ultrasonic actuator drives the microprobe at a mechanical resonance frequency of the microprobe.

5. The ultrasonic viscosity sensor of claim 1, wherein the ultrasonic actuator has a predetermined cross-section for amplifying motion imparted to the microprobe.

6. The ultrasonic viscosity sensor of claim 1, wherein the ultrasonic waves have frequencies between 10 Hz and 20 kHz.

7. The ultrasonic viscosity sensor of claim 1, wherein the ultrasonic waves have frequencies between 20 kHz and 500 kHz.

8. The ultrasonic viscosity sensor of claim 1, wherein the ultrasonic waves have frequencies between 500 kHz and 10 MHz.

9. The ultrasonic viscosity sensor of claim 1, wherein when the amplitude is equal to a first amplitude, the viscosity is equal to a first viscosity, wherein when the amplitude is lower than the first amplitude, the viscosity is higher than the first viscosity, and wherein when the amplitude is higher than the first amplitude the viscosity is lower than the first viscosity.

10. The ultrasonic viscosity sensor of claim 9, wherein the amplitude is determined by at least two strain gauges or piezoresistors located near a junction of the ultrasonic actuator and the microprobe, and wherein at least one of the strain gauges or piezoresistors determines the amplitude.

11. The ultrasonic viscosity sensor of claim 10, wherein at least one of the strain gauges or piezoresistors is a polysilicon resistor.

12. The ultrasonic viscosity sensor of claim 10, wherein at least one of the strain gauges or piezoresistors has a nominal resistance of about 10 k$\Omega$.

13. The ultrasonic viscosity sensor of claim 1, wherein spaces between the patterned electrodes are in steps to enable determination of the immersion depth by determining one or more positions along the microprobe where the fluid is present, wherein for each position where the fluid is present a different capacitance is caused between the conductive traces on the patterned electrodes compared to when the fluid is not present.

14. The ultrasonic viscosity sensor of claim 1, further comprising circuitry for determining the immersion depth and the capacitance, wherein the viscosity of the fluid is determined from the immersion depth of the microprobe and the amplitude.

15. The ultrasonic viscosity sensor of claim 1, further comprising:
   a horn, wherein the microprobe includes at least one polysilicon strain gauge or piezoresistor connected in a Wheatstone bridge configuration.

16. The ultrasonic viscosity sensor of claim 1, wherein the ultrasonic waves have frequencies between 500 kHz and 10 MHz.

17. The ultrasonic viscosity sensor of claim 1, further comprising: at least one multi-sensor microprobe.

18. The ultrasonic viscosity sensor of claim 17, wherein the at least one multi-sensor microprobe comprises a plurality of strain gauges or piezoresistors.

19. The ultrasonic viscosity sensor of claim 1, wherein the microprobe comprises a plurality of capacitance-based immersion depth sensors.

20. The ultrasonic viscosity sensor of claim 1, wherein the patterned electrodes comprise platinum, gold, silver, or other conductor of electrical current.

21. The ultrasonic viscosity sensor of claim 1, wherein the substrate and horn comprise silicon or other semiconductor material, FR4 or other circuit board material, or plastic.

22. A method for using a microprobe having patterned electrodes to determine a viscosity of a fluid, the method comprising:
   producing ultrasonic waves by an ultrasonic actuator, wherein the ultrasonic waves have a corresponding frequency that is resonant at a microprobe;
   coupling the ultrasonic waves to the fluid via the microprobe, wherein at least an amplitude of the ultrasonic waves at the microprobe determines the viscosity of the fluid, and wherein the microprobe includes patterned electrodes for determining an immersion depth of the microprobe in the fluid from a capacitance between conductive traces on the patterned electrodes;
   determining a viscous damping of non-linear flexural vibrations of the microprobe; and
   determining a shear decay length ($\delta$) at an actuator resonance, wherein $\delta$ is determined by at least the viscosity of the fluid, a density of the fluid, and a frequency of the ultrasonic waves.

23. The method of claim 22, wherein the non-linear flexural vibrations of the microprobe comprise longitudinal and flexural oscillating motions.

24. The method of claim 22, wherein measuring viscous damping comprises measuring viscous damping at multiple frequencies.

25. The method of claim 24, wherein a first of the multiple frequencies is a longitudinal mode frequency and a second of the multiple frequencies is at least one microprobe resonance frequency.

26. The method of claim 22, comprising calibrating the immersion depth.

27. The method of claim 26, wherein the calibrating comprises determining capacitances at predetermined steps.

28. The method of claim 22, wherein the shear decay length ($\delta$) is expressed as:

$$\delta = \left(\frac{2\eta}{\omega\rho}\right)^{\frac{1}{2}},$$

and wherein $\eta$ is a fluid viscosity, $\rho$ is the density, and $\omega=2\pi f$ is the angular frequency of the ultrasonic waves.

29. The method of claim 22, further comprising determining the viscosity of the fluid at different shear rates.

30. The method of claim 29, further comprising varying a piezoelectric transducer (PZT) actuation voltage.

31. The method of claim 22, further comprising: determining a coagulation time of the fluid.

32. A method for operating a microprobe having patterned electrodes to determine a viscosity of a fluid comprising:
producing ultrasonic waves by an ultrasonic actuator, wherein the ultrasonic waves have a corresponding frequency that is resonant at a microprobe;
coupling the ultrasonic waves to the fluid via the microprobe, wherein at least an amplitude of the ultrasonic waves at the microprobe determines the viscosity of the fluid, and wherein the microprobe includes patterned electrodes for determining an immersion depth of the microprobe in the fluid from a capacitance between conductive traces on the patterned electrodes; and
determining a shear decay length ($\delta$) at an actuator resonance, wherein $\delta$ is determined by at least the viscosity of the fluid, a density of the fluid, and a frequency of the ultrasonic waves.

33. The method of claim 32, wherein the shear decay length ($\delta$) is expressed as:

$$\delta = \left(\frac{2\eta}{\omega\rho}\right)^{\frac{1}{2}},$$

wherein $\eta$ is a fluid viscosity, $\rho$ is the density, and $\omega=2\pi f$ is the angular frequency of the ultrasonic waves.

* * * * *